United States Patent
Haig et al.

(10) Patent No.: US 9,402,613 B2
(45) Date of Patent: Aug. 2, 2016

(54) EXPANDABLE THORACIC ACCESS PORT

(71) Applicant: Covidien LP, Mansfield, MA (US)

(72) Inventors: Fiona Middlemiss Haig, Boston, MA (US); Cormac O'Prey, Hertfordshire (GB); Valerie Anne Scott, Cambridge (GB); Charlotte Adele Clark, Cambridge (GB)

(73) Assignee: Covidien LP, Mansfield, MA (US)

( * ) Notice: Subject to any disclaimer, the term of this patent is extended or adjusted under 35 U.S.C. 154(b) by 100 days.

(21) Appl. No.: 14/264,502

(22) Filed: Apr. 29, 2014

(65) Prior Publication Data

US 2014/0235952 A1    Aug. 21, 2014

Related U.S. Application Data

(62) Division of application No. 13/005,611, filed on Jan. 13, 2011, now Pat. No. 8,777,849.

(60) Provisional application No. 61/304,083, filed on Feb. 12, 2010.

(51) Int. Cl.
*A61B 1/32* (2006.01)
*A61B 17/02* (2006.01)
(Continued)

(52) U.S. Cl.
CPC ......... *A61B 17/0281* (2013.01); *A61B 17/0206* (2013.01); *A61B 17/3423* (2013.01); *A61B 17/3431* (2013.01); *A61B 17/3439* (2013.01); *A61B 2017/00946* (2013.01);
(Continued)

(58) Field of Classification Search
CPC ............. A61B 17/0218; A61B 17/025; A61B 17/0206; A61B 1/32; A61B 17/3423; A61B 17/00234; A61B 17/02; A61B 17/0293; A61B 17/0231; A61B 17/3431; A61B 2017/0237; A61B 2017/0212; A61B 2017/3425; A61B 2017/3427; A61B 2017/3429

See application file for complete search history.

(56) References Cited

U.S. PATENT DOCUMENTS 1,780,912 A   11/1930   Gau
1,810,466 A   6/1931    Deutsch
2,313,164 A   3/1943    Nelson
(Continued)

FOREIGN PATENT DOCUMENTS

DE       10001695 A1    2/2001
DE     102009014527 A1  9/2010
(Continued)

OTHER PUBLICATIONS

EP Search Report 11 25 0163 dated Jun. 7, 2011.
(Continued)

*Primary Examiner* — Jacqueline Johanas

(57) ABSTRACT

A surgical access assembly includes a body having first and second body members. Each body member has an opposed side and an outer side. The body members are coupled to one another by a connector and are moveable with respect to one another between an approximated position and a spread position wherein the opposed sides are flexed outwardly and apart from one another to define a passageway therebetween. A flexible membrane is coupled to the first and second body members and extends therefrom such that translating the flexible membrane radially outwardly moves the body members from the approximated position to the spread position.

24 Claims, 5 Drawing Sheets

(51) Int. Cl.
    *A61B 17/34*          (2006.01)
    *A61B 17/00*          (2006.01)

(52) U.S. Cl.
    CPC .. *A61B 2017/348* (2013.01); *A61B 2017/3427* (2013.01); *A61B 2017/3484* (2013.01)

(56) References Cited

U.S. PATENT DOCUMENTS

| | | | |
|---|---|---|---|
| 2,541,516 A | 2/1951 | Ivory et al. | |
| 2,812,758 A | 11/1957 | Blumenschein | |
| 3,332,417 A * | 7/1967 | Blanford | A61B 17/0293 128/850 |
| 3,522,800 A * | 8/1970 | Lesser | A61B 17/02 128/850 |
| 3,782,370 A | 1/1974 | McDonald | |
| 3,807,393 A | 4/1974 | McDonald | |
| 3,965,890 A | 6/1976 | Gauthier | |
| 4,130,113 A | 12/1978 | Graham | |
| 4,263,899 A | 4/1981 | Burgin | |
| 4,412,532 A * | 11/1983 | Anthony | A61B 17/0231 600/206 |
| 4,553,537 A | 11/1985 | Rosenberg | |
| 5,007,900 A | 4/1991 | Picha et al. | |
| 5,052,374 A | 10/1991 | Alvarez-Jacinto | |
| 5,080,088 A | 1/1992 | LeVahn | |
| 5,125,396 A | 6/1992 | Ray | |
| 5,169,387 A | 12/1992 | Kronner | |
| 5,231,974 A | 8/1993 | Giglio et al. | |
| 5,232,451 A | 8/1993 | Freitas et al. | |
| 5,269,754 A | 12/1993 | Rydell | |
| 5,279,575 A | 1/1994 | Sugarbaker | |
| 5,330,501 A | 7/1994 | Tovey et al. | |
| 5,346,484 A | 9/1994 | Van Lindert | |
| 5,391,156 A | 2/1995 | Hildwein et al. | |
| 5,437,683 A | 8/1995 | Neumann et al. | |
| 5,445,615 A | 8/1995 | Yoon | |
| 5,460,170 A | 10/1995 | Hammerslag | |
| 5,480,410 A | 1/1996 | Cuschieri et al. | |
| 5,490,843 A | 2/1996 | Hildwein et al. | |
| 5,503,617 A | 4/1996 | Jako | |
| 5,520,610 A | 5/1996 | Giglio et al. | |
| 5,524,644 A | 6/1996 | Crook | |
| 5,556,385 A | 9/1996 | Andersen | |
| 5,562,677 A | 10/1996 | Hildwein et al. | |
| 5,653,705 A | 8/1997 | de la Torre et al. | |
| 5,697,891 A | 12/1997 | Hori | |
| 5,728,103 A | 3/1998 | Picha et al. | |
| 5,755,660 A | 5/1998 | Tyagi | |
| 5,755,661 A | 5/1998 | Schwartzman | |
| 5,772,583 A | 6/1998 | Wright et al. | |
| 5,776,110 A | 7/1998 | Guy et al. | |
| 5,779,629 A | 7/1998 | Hohlen | |
| 5,788,630 A | 8/1998 | Furnish | |
| 5,803,921 A | 9/1998 | Bonadio | |
| 5,810,721 A | 9/1998 | Mueller et al. | |
| 5,846,193 A | 12/1998 | Wright | |
| 5,875,782 A | 3/1999 | Ferrari et al. | |
| 5,879,291 A | 3/1999 | Kolata et al. | |
| 5,906,577 A | 5/1999 | Beane et al. | |
| 5,908,382 A | 6/1999 | Koros et al. | |
| 5,931,778 A | 8/1999 | Furnish | |
| 5,935,107 A | 8/1999 | Taylor et al. | |
| 5,944,736 A * | 8/1999 | Taylor et al. | 606/198 |
| 5,951,466 A * | 9/1999 | Segermark et al. | 600/225 |
| 5,951,467 A | 9/1999 | Picha et al. | |
| 5,957,835 A | 9/1999 | Anderson et al. | |
| 5,967,972 A | 10/1999 | Santilli et al. | |
| 5,993,385 A | 11/1999 | Johnston et al. | |
| 6,024,736 A | 2/2000 | de la Torre et al. | |
| 6,033,362 A | 3/2000 | Cohn | |
| 6,033,425 A | 3/2000 | Looney et al. | |
| 6,033,426 A * | 3/2000 | Kaji | 606/213 |
| 6,036,641 A | 3/2000 | Taylor et al. | |
| 6,048,309 A * | 4/2000 | Flom et al. | 600/234 |
| 6,074,380 A | 6/2000 | Byrne et al. | |
| 6,113,535 A | 9/2000 | Fox et al. | |
| 6,120,436 A | 9/2000 | Anderson et al. | |
| 6,132,370 A | 10/2000 | Furnish et al. | |
| 6,142,935 A | 11/2000 | Flom et al. | |
| 6,159,231 A | 12/2000 | Looney et al. | |
| 6,162,172 A | 12/2000 | Cosgrove et al. | |
| 6,231,506 B1 | 5/2001 | Hu et al. | |
| 6,254,533 B1 | 7/2001 | Fadem et al. | |
| 6,254,534 B1 | 7/2001 | Butler et al. | |
| 6,283,912 B1 | 9/2001 | Hu et al. | |
| 6,309,349 B1 | 10/2001 | Bertolero et al. | |
| 6,312,377 B1 | 11/2001 | Segermark et al. | |
| 6,331,158 B1 | 12/2001 | Hu et al. | |
| 6,354,995 B1 | 3/2002 | Hoftman et al. | |
| 6,361,492 B1 | 3/2002 | Santilli | |
| 6,382,211 B1 | 5/2002 | Crook | |
| 6,443,957 B1 | 9/2002 | Addis | |
| 6,450,983 B1 | 9/2002 | Rambo | |
| 6,458,079 B1 | 10/2002 | Cohn et al. | |
| 6,488,620 B1 * | 12/2002 | Segermark | A61B 17/0293 600/208 |
| 6,500,116 B1 | 12/2002 | Knapp | |
| 6,517,563 B1 | 2/2003 | Paolitto et al. | |
| 6,547,725 B1 | 4/2003 | Paolitto et al. | |
| 6,585,442 B2 | 7/2003 | Brei et al. | |
| 6,599,240 B2 | 7/2003 | Puchovsky et al. | |
| 6,599,292 B1 | 7/2003 | Ray | |
| 6,616,605 B2 | 9/2003 | Wright et al. | |
| 6,647,985 B1 * | 11/2003 | Prywes | 128/853 |
| 6,652,454 B2 | 11/2003 | Hu et al. | |
| 6,723,044 B2 | 4/2004 | Pulford et al. | |
| 6,730,021 B2 | 5/2004 | Vassiliades, Jr. et al. | |
| 6,730,022 B2 | 5/2004 | Martin et al. | |
| 6,746,396 B1 | 6/2004 | Segermark et al. | |
| 6,746,467 B1 | 6/2004 | Taylor et al. | |
| 6,814,078 B2 | 11/2004 | Crook | |
| 6,814,700 B1 | 11/2004 | Mueller et al. | |
| 6,840,951 B2 | 1/2005 | de la Torre et al. | |
| 6,846,287 B2 | 1/2005 | Bonadio et al. | |
| 6,958,037 B2 | 10/2005 | Ewers et al. | |
| 7,033,319 B2 | 4/2006 | Pulford et al. | |
| 7,052,454 B2 | 5/2006 | Taylor | |
| 7,144,368 B2 | 12/2006 | Larson et al. | |
| 7,147,599 B2 | 12/2006 | Phillips et al. | |
| 7,179,225 B2 | 2/2007 | Shluzas et al. | |
| 7,195,592 B2 | 3/2007 | Ravikumar et al. | |
| 7,220,228 B2 | 5/2007 | Hu et al. | |
| 7,226,451 B2 | 6/2007 | Shluzas et al. | |
| 7,229,408 B2 | 6/2007 | Douglas et al. | |
| 7,238,154 B2 | 7/2007 | Ewers et al. | |
| 7,261,688 B2 | 8/2007 | Smith et al. | |
| 7,270,632 B2 | 9/2007 | Santilli | |
| 7,300,399 B2 | 11/2007 | Bonadio et al. | |
| 7,344,495 B2 | 3/2008 | Ravikumar et al. | |
| 7,387,126 B2 | 6/2008 | Cox et al. | |
| 7,393,322 B2 | 7/2008 | Wenchell | |
| 7,507,202 B2 | 3/2009 | Schoellhorn | |
| 7,507,235 B2 | 3/2009 | Keogh et al. | |
| 7,537,564 B2 * | 5/2009 | Bonadio et al. | 600/208 |
| 7,540,839 B2 | 6/2009 | Butler et al. | |
| 7,559,893 B2 | 7/2009 | Bonadio et al. | |
| 7,566,302 B2 | 7/2009 | Schwer | |
| 7,585,277 B2 | 9/2009 | Taylor et al. | |
| 7,594,888 B2 | 9/2009 | Raymond et al. | |
| 7,650,887 B2 | 1/2010 | Nguyen et al. | |
| 7,758,500 B2 * | 7/2010 | Boyd | A61B 17/0293 600/206 |
| 8,777,849 B2 | 7/2014 | Haig et al. | |
| 8,857,440 B2 * | 10/2014 | Gundlapalli et al. | 128/850 |
| 2001/0002429 A1 | 5/2001 | Hu et al. | |
| 2001/0020121 A1 | 9/2001 | Hu et al. | |
| 2001/0041827 A1 | 11/2001 | Spence et al. | |
| 2002/0004628 A1 | 1/2002 | Hu et al. | |
| 2002/0095139 A1 | 7/2002 | Keogh et al. | |
| 2002/0099269 A1 | 7/2002 | Martin et al. | |
| 2002/0099271 A1 | 7/2002 | Knapp | |
| 2002/0137989 A1 | 9/2002 | Clem et al. | |
| 2003/0191371 A1 | 10/2003 | Smith et al. | |

(56) References Cited

U.S. PATENT DOCUMENTS

| | | |
|---|---|---|
| 2004/0049099 A1 | 3/2004 | Ewers et al. |
| 2004/0054353 A1* | 3/2004 | Taylor ............................ 606/1 |
| 2004/0059192 A1 | 3/2004 | Cartier et al. |
| 2004/0225195 A1 | 11/2004 | Spence et al. |
| 2004/0267096 A1* | 12/2004 | Caldwell et al. ............. 600/213 |
| 2005/0096508 A1 | 5/2005 | Valentini et al. |
| 2005/0137460 A1 | 6/2005 | Bertolero et al. |
| 2005/0171403 A1 | 8/2005 | Paolitto et al. |
| 2005/0228232 A1 | 10/2005 | Gillinov et al. |
| 2005/0267336 A1 | 12/2005 | Bertolero et al. |
| 2005/0283050 A1* | 12/2005 | Gundlapalli et al. ......... 600/208 |
| 2006/0004261 A1 | 1/2006 | Douglas |
| 2006/0089537 A1 | 4/2006 | Schoellhorn |
| 2006/0106416 A1 | 5/2006 | Raymond et al. |
| 2006/0129165 A1* | 6/2006 | Edoga et al. .................. 606/108 |
| 2006/0149137 A1* | 7/2006 | Pingleton et al. ............. 600/208 |
| 2006/0149306 A1 | 7/2006 | Hart et al. |
| 2006/0155170 A1 | 7/2006 | Hanson et al. |
| 2007/0027364 A1 | 2/2007 | Schwer |
| 2007/0073110 A1 | 3/2007 | Larson et al. |
| 2007/0167980 A1 | 7/2007 | Figulla et al. |
| 2007/0299314 A1 | 12/2007 | Bertolero et al. |
| 2008/0132766 A1 | 6/2008 | Dant et al. |
| 2008/0234550 A1 | 9/2008 | Hawkes et al. |
| 2009/0062618 A1 | 3/2009 | Drew et al. |
| 2009/0105655 A1 | 4/2009 | DeSantis et al. |
| 2009/0204067 A1 | 8/2009 | Abu-Halawa |
| 2009/0265941 A1 | 10/2009 | Kurrus |
| 2009/0299148 A1 | 12/2009 | White et al. |
| 2009/0326469 A1 | 12/2009 | Rockrohr |
| 2010/0168522 A1 | 7/2010 | Wenchell et al. |
| 2010/0210916 A1 | 8/2010 | Hu et al. |
| 2010/0234689 A1 | 9/2010 | Wagner et al. |
| 2010/0261970 A1 | 10/2010 | Shelton, IV et al. |
| 2010/0298646 A1 | 11/2010 | Stellon et al. |
| 2011/0021879 A1 | 1/2011 | Hart et al. |
| 2011/0201892 A1* | 8/2011 | Haig ................... A61B 17/0206 600/206 |
| 2011/0201893 A1* | 8/2011 | O'Prey ............... A61B 17/3423 600/208 |
| 2011/0201894 A1* | 8/2011 | O'Prey ............... A61B 17/0293 600/219 |
| 2011/0201896 A1* | 8/2011 | O'Prey ............... A61B 17/0206 600/228 |
| 2011/0319719 A1* | 12/2011 | O'Prey ............... A61B 17/0206 600/206 |

FOREIGN PATENT DOCUMENTS

| | | |
|---|---|---|
| EP | 0177177 A2 | 4/1986 |
| EP | 2179669 A2 | 4/2010 |
| EP | 2228014 A1 | 9/2010 |
| EP | 2228024 A1 | 9/2010 |
| EP | 2238931 A1 | 10/2010 |
| EP | 2417922 A1 | 2/2012 |
| EP | 2422725 A2 | 2/2012 |
| EP | 2462883 A1 | 6/2012 |
| GB | 2275420 A | 8/1994 |
| JP | H10507653 A | 7/1998 |
| WO | 95/00197 A1 | 1/1995 |
| WO | 95/15715 A1 | 6/1995 |
| WO | 9605773 A1 | 2/1996 |
| WO | 01/08563 A2 | 2/2001 |
| WO | 03/034908 A2 | 5/2003 |
| WO | 2005089655 A1 | 9/2005 |
| WO | 2010042913 A2 | 4/2010 |
| WO | 2010/136805 A1 | 12/2010 |
| WO | 2011/079374 A1 | 7/2011 |

OTHER PUBLICATIONS

European Search Report EP 11 25 0719 dated Nov. 16, 2011.
EP Search Report EP 11 18 9987 dated Feb. 15, 2012.
EP Search Report 11250164 dated Aug. 6, 2011.
EP Search Report EP 12160423.5 dated Jun. 25, 2012.
EP Search Report EP 12 15 4733 dated Jan. 14, 2014.
Japanese Office Action dated Feb. 28, 2014.
Chinese Office Action dated Mar. 25, 2014 issued in Chinese Appln No. 201110089164.2.
Chinese Office Action dated Feb. 2, 2015 issued in Chinese Appln. No. 201110089164.

* cited by examiner

EXPANDABLE THORACIC ACCESS PORT

This application is a divisional of U.S. patent application Ser. No. 13/005,611, filed Jan. 13, 2011, which claims priority from provisional application Ser. No. 61/304,083, filed Feb. 12, 2010, each of the above-identified applications being incorporated herein by reference.

BACKGROUND

1. Technical Field

The present disclosure relates generally to devices and techniques for performing surgical procedures. More particularly, the present disclosure relates to an access device for minimally invasive surgery.

2. Background of the Related Art

In an effort to reduce trauma and recovery time, many surgical procedures are performed through small openings in the skin, such as an incision or a natural body orifice. For example, these procedures include laparoscopic procedures, which are generally performed within the confines of a patient's abdomen, and thoracic procedures, which are generally performed within a patient's chest cavity.

Specific surgical instruments have been developed for use during such minimally invasive surgical procedures. These surgical instruments typically include an elongated shaft with operative structure positioned at a distal end thereof, such as graspers, clip appliers, specimen retrieval bags, etc.

During minimally invasive procedures, the clinician creates an opening in the patient's body wall, oftentimes by using an obturator or trocar, and thereafter positions an access assembly within the opening. The access assembly includes a passageway extending therethrough to receive one or more of the above-mentioned surgical instruments for positioning within the internal work site, e.g. the body cavity.

During minimally invasive thoracic procedures, an access assembly is generally inserted into a space located between the patient's adjacent ribs that is known as the intercostal space, and then surgical instruments can be inserted into the internal work site through the passageway in the access assembly.

In the interests of facilitating visualization, the introduction of certain surgical instruments, and/or the removal of tissue specimens during minimally invasive thoracic procedures, it may be desirable to spread tissue adjacent the ribs defining the intercostal space. Additionally, during these procedures, firm, reliable placement of the access assembly is desirable to allow the access assembly to withstand forces that are applied during manipulation of the instrument(s) inserted therethrough. However, reducing patient trauma during the procedure, discomfort during recovery, and the overall recovery time remain issues of importance. Thus, there exists a need for thoracic access ports which minimize post operative patient pain while enabling atraumatic retraction of tissue and which do not restrict access to the body cavity, as well as facilitates removal of tissue specimens from the body cavity.

SUMMARY

In accordance with the present disclosure, a surgical access assembly, or access port, for positioning within an opening in tissue is provided. In one aspect, the surgical access assembly includes a body having first and second body members. Each body member includes an opposed side and an outer side. The first and second body members are coupled to one another by a connector and are moveable with respect to one another between an approximated position and a spread position. In the approximated position, the opposed sides of the first and second body members are closer to one another. In the spread position, the opposed sides of the first and second body members are flexed outwardly and apart from one another to define a passageway therebetween. A flexible membrane is coupled to the first and second body members and extends therefrom. The flexible membrane is configured such that translating the flexible membrane radially outwardly moves the body members from the approximated position to the spread position.

In one embodiment, the flexible membrane is coupled to an adjustable member at a proximal end thereof. The adjustable member can be configured to tension the flexible membrane to move the body members between the approximated and spread positions. Releasing the tension on the flexible membrane can allow the body members to return to the approximated position. The adjustable member may include an adjustable ring coupled to the flexible membrane. The adjustable ring may be selectively adjustable between a first position defining a minimum diameter of the ring and a second position defining a larger diameter of the ring.

In some embodiments, one or more ribbons are coupled to the connector to remove the access assembly from the body cavity through the incision after completion of the procedure. The ribbon can also in some embodiments be used for manipulating the positioning and orientation of the access assembly.

In some embodiments, an outwardly facing surface of each of the body members defines a curved cross-sectional configuration. Each of the body members may also increase in thickness from the opposed sides to the outer sides thereof.

The connector can define a generally horseshoe shaped configuration and can be connected to the leading ends of the first and second body members toward the outer sides thereof.

Cushioning can be disposed on the outwardly facing surfaces of the body members to protect surrounding tissue when the access assembly is disposed through an opening in tissue.

The body members in some embodiments can be biased toward the approximated position.

In another aspect, the present disclosure provides a surgical access assembly for positioning within an opening in tissue comprising a body including first and second body members, each body member including a leading end, a trailing end and first and second sides. The first and second body members are coupled to one another and moveable with respect to one another between an approximated position, wherein a side of the first and second body members are closer to one another, and a spread position, wherein the first sides of the first and second body members are spaced further apart from one another to define a passageway therebetween. The body members are insertable into the incision with the leading end oriented toward the incision, and the body member is subsequently pivotable to a transverse position, with the passageway defined between the body members in the transverse position of the body members.

A flexible membrane extending from the first and second body members graspable by a user to move the body members to the transverse position and/or to move the body members to the spread position can be provided. A locking member can be provided to selectively lock the body members in an intermediate position between the approximated and spread positions.

In another aspect, the present disclosure provides a surgical access assembly for positioning within an opening in tissue comprising a body including first and second body members, each body member including an opposed side, a leading end and a trailing end. The first and second body members are coupled to one another and moveable with respect to one another between an approximated position, wherein the opposed sides of the first and second body members are closer to one another, and a spread position, wherein the opposed sides of the first and second body members are rotated outwardly away from each other to define a passageway therebetween.

An outer surface of each body member can be curved and can engage an inner surface of the tissue within the incision. A cushioning member can be positioned on the outer surface of the body members. A flexible material can extend from the body members movable to rotate the body members outwardly.

A method of accessing an internal cavity of a patient is also provided in accordance with another aspect of the present disclosure. The method includes forming an opening in the patient's tissue and providing an access assembly. Next, with the access assembly in the approximated position, the leading end of the access assembly is inserted through the opening in the patient's tissue such that the body of the access assembly is positioned within an intercostal space defined between adjacent ribs of the patient and such that the flexible membrane extends proximally from the opening in tissue. The access assembly is then rotated such that the adjacent opposed sides are aligned with the opening in tissue. Next, the flexible membrane is translated radially outwardly, moving the body members from the approximated position to the spread position and expanding the intercostal space to create a passageway into the patient's internal body cavity.

In one embodiment, one or more ribbons can be used to facilitate translation and/or rotation of the access assembly.

In another embodiment, the method further includes introducing surgical instrumentation and/or a tissue specimen through the access assembly.

The method can further include releasing the tension on the flexible member to allow the access assembly to move from the spread position to the approximated position. The access assembly can then in some embodiments be rotated such that the leading end is positioned adjacent the opening in tissue and can then be translated proximally via the leading end, e.g., by pulling one of the ribbons coupled to the leading end, to remove the access assembly from the opening in tissue.

BRIEF DESCRIPTION OF THE DRAWINGS

Various embodiments of the subject access port are described herein with reference to the drawings wherein.

DETAILED DESCRIPTION

Figure 1:
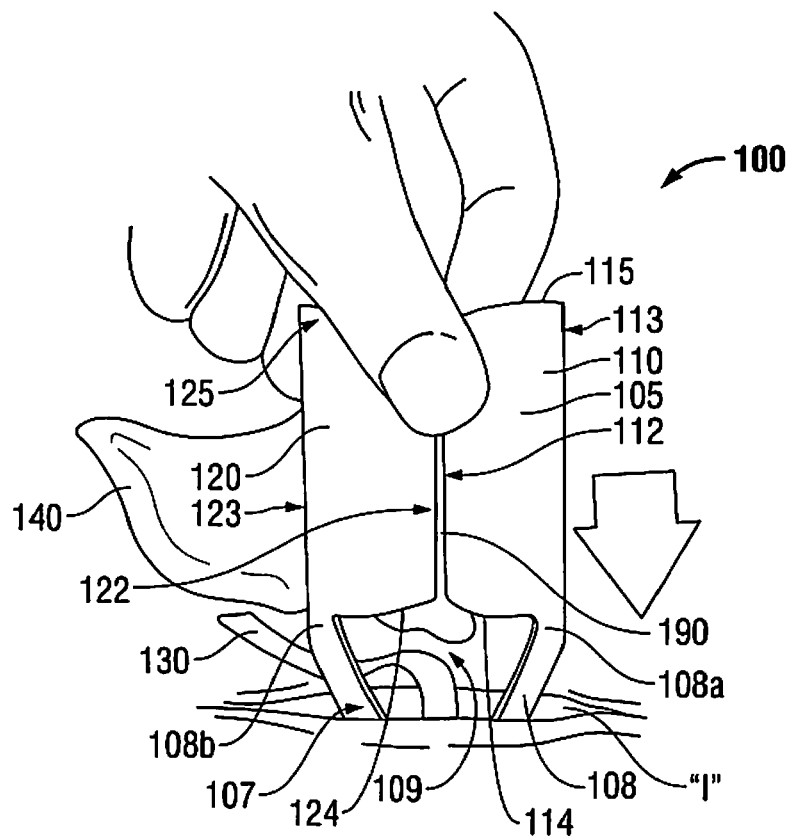
FIG. 1 is a side view of an access port according to the present disclosure shown being inserted into an incision in tissue.

Various embodiments of the presently disclosed access assembly, or access port, and methods of using the same, will now be described in detail with reference to the drawings wherein like references numerals identify similar or identical elements. In the drawings, and in the following description, the term "proximal" should be understood as referring to the end of the access port, or component thereof, that is closer to the clinician during proper use, while the term "distal" should be understood as referring to the end that is further from the clinician, as is traditional and conventional in the art. Additionally, use of the term "tissue" hereinbelow should be understood to encompass both the patient's ribs, and any surrounding tissues. It should be also be understood that the term "minimally invasive procedure" is intended to include surgical procedures through small openings/incisions performed within a confined space such as the thoracic cavity or abdominal cavity.

Referring now to FIGS. 1-5B, the presently disclosed surgical access port is shown generally identified by the reference numeral 100. In the embodiment of FIGS. 1-5B, the access port 100 is depicted as a thoracic port 100 that is configured and dimensioned for insertion into the intercostal space located between the adjacent ribs "R" (FIG. 3) of a patient in order to allow for the insertion and manipulation of one or more surgical instruments within the thoracic cavity. However, it is also envisioned that access port 100 may be configured and dimensioned to provide access to a variety of other internal body cavities and/or tissues. Further, access port 100 may be formed from any suitable biocompatible material of strength suitable for the purpose described herein, including, but not being limited to, polymeric materials.

The access port 100 is configured and dimensioned to extend into a body cavity, e.g., the thoracic cavity "T" (FIGS. 3 and 6), through the intercostal space, and generally includes a body 105 having a horseshoe shaped leading end 107 and first and second body members 110, 120 interconnected by the horseshoe shaped leading end 107. A ribbon 130 is attached to the horseshoe shaped leading end 107 to facilitate removal of the access port 100 from the cavity "T" and through incision "I" after the procedure. A flexible membrane 140 is attached at a distal end 142 thereof to opposed (inner) sides 112 and 122 of the first and second body members 110, 120, respectively, and is attached at a proximal end 144 to an adjustable ring 150. Access port 100 is moveable between a closed, or approximated position for insertion and removal, and an open, or spaced apart position wherein a passageway 190 (FIG. 3) extends therethrough to provide access to the internal body cavity.

First and second body members 110, 120, include an outer side 113, 123, a leading end 114, 124 and a trailing end 115, 125, respectively. In the approximated, or closed position of access port 100, shown in FIG. 1, opposed sides 112, 122 of body members 110, 120, respectively, are positioned closer to each other, and preferably adjacent each other. End 108a of horseshoe shaped connector 108 is attached to leading end 114 of body member 110, and end 108b of horseshoe shaped connector 108 is attached to leading end 124 of body member 120. An opening 109 is defined between horseshoe shaped connector 108 and the leading ends 114, 124 of body members 110, 120, respectively.

Figure 3:
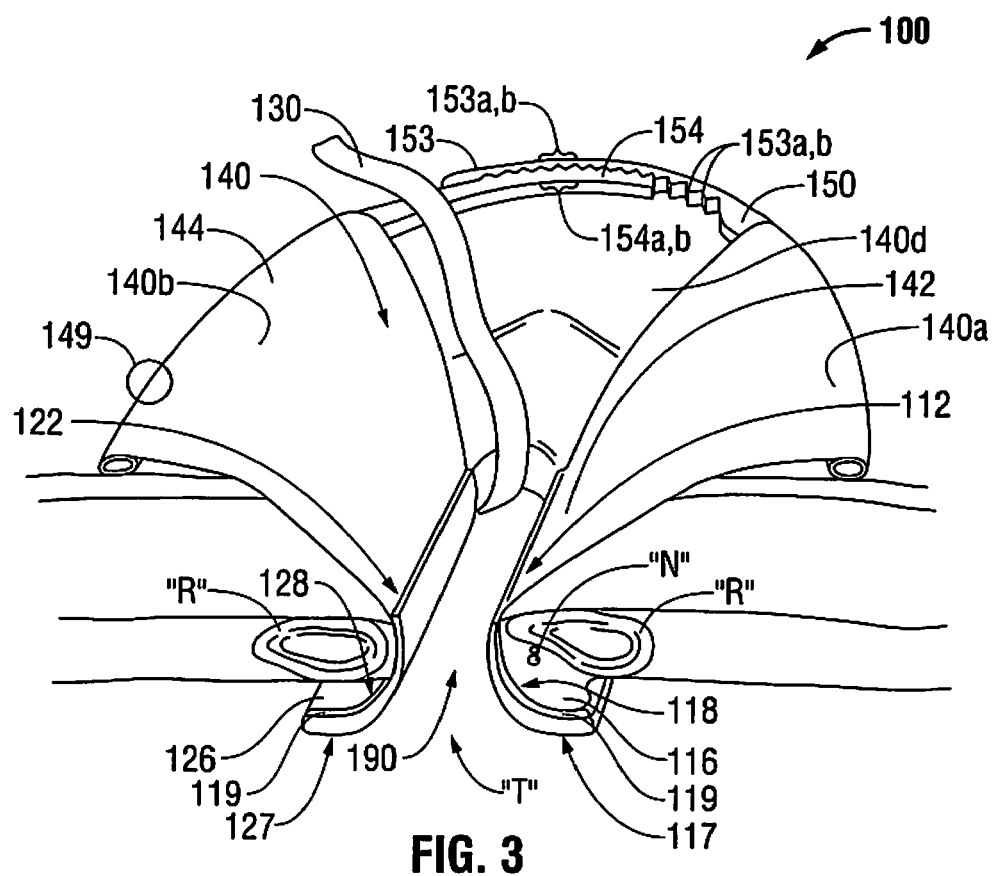
FIG. 3 is a side, cross-sectional view of the access port of FIG. 1 disposed in the spread position.

Body members 110, 120 of access port 100 may be formed from a semi-rigid material to give access port 100 structural support while still allowing for some degree of flexibility. At least a portion of body members 110, 120 can be transparent to permit visualization through the access port 100 and into the surgical site. Body members 110, 120 may increase in thickness from their respective opposed sides 112, 122 to their respective outer sides 113, 123, as best shown in FIG. 3, and/or may include cushioning 119 (FIG. 3) disposed adjacent outer sides 113, 123 and extending along outwardly facing surfaces 116, 126 of body members 110, 120, respectively. This increased thickness and/or cushioning 119 helps protect surrounding tissue, e.g., ribs "R" and nerves "N," during the insertion and removal of surgical instrumentation and/or body tissue through the access port 100. As can be appreciated, the increased thickness of body members 110, 120 also allows the outer sides 113, 123 to be more rigid, or less flexible, than the opposed sides 112, 122 of body members 110, 120, respectively. As will become more apparent below, in a preferred embodiment, body members 110, 120 have increasing flexibility from the outer sides 113, 123 to the opposed sides 112, 122 such that the opposed sides 112, 122 may be moved apart from one another to create a passageway 190 extending through access port 100.

Access port 100 may be biased toward the approximated position wherein body members 110, 120 are positioned closer to, and preferably adjacent, one another. In this embodiment, if the body members 110, 120 are flexed to the open position and are not retained in the open position by a locking mechanism, body members 110, 120 would return under the bias to the approximated or closed position.

Each of the body members 110, 120 may define a similarly arcuate or curved profile on one or both surfaces, as viewed from either the leading ends 114, 124 or trailing ends 115, 125 of body members 110, 120, respectively. In other words, the outwardly facing surfaces 116, 126 of body members 110, 120, respectively, may define a generally convex configuration and/or the inwardly facing surfaces 117, 127 of body members 110, 120, respectively, may define a generally concave configuration. Accordingly, a saddle 118, 128 (FIG. 3) may be formed within each of the outwardly facing surfaces 116, 126 of body members 110, 120, respectively, of access port 100. As can be appreciated, saddles 118, 128 are relatively shallow when access port 100 is disposed in the approximated or closed position (FIG. 1). However, upon movement of access port 100 to the open, or spaced apart position (FIG. 3), saddles 118, 128 become more defined for seating ribs "R" therein. Correspondingly, as opposed sides 112, 122 are moved apart from one another, the outwardly facing surfaces 116, 126 of body portions 110, 120, respectively, become more convex, while the inwardly facing surfaces 117, 127 become more concave.

As best shown in FIG. 3, flexible membrane 140 is generally funnel shaped when tensioned and is coupled at distal end 142 thereof to opposed sides 112, 122 of body members 110, 120, respectively. More specifically, a first section 140a of flexible membrane 140 is mechanically coupled to opposed side 112 along the length of opposed side 112 of body member 110 and a second section 140b of flexible membrane is similarly mechanically coupled to opposed side 122 along the length of opposed side 122 of body member 120. A pair of end sections 140d of flexible membrane 140 connect the first and second sections 140a and 140b of flexible membrane 140 to one another, thereby defining the completed funnel shape, as shown in FIG. 3. In other words, flexible membrane 140 creates a funnel-shaped passageway 190 from the proximal end 144 thereof to the distal end 142 thereof. The funnel-shaped membrane 140 thus extends distally with the body members 110, 120 forming the distal-most portion of the funnel. As can be appreciated, the funnel is more conically shaped when body members 110, 120 are in the approximated position, i.e., where opposed sides 112, 122 of body members 110, 120 are adjacent one another, while the funnel is more cylindrically shaped when body members 110, 120 are in the open position, i.e., where opposed sides 112, 122 are spaced apart from one another.

It is envisioned that flexible membrane 140 is configured for soft tissue retraction. More particularly, it is envisioned that flexible membrane 140 has a sufficient elasticity to permit retraction of a wide range of tissue thicknesses since there may be a wide range of tissue thicknesses among different patients. It is also envisioned that flexible membrane 140 is of sufficient strength to properly retract body members 110, 120 when tensioned, to resist accidental puncture by sharp surgical instrumentation, and to resist tearing. Additionally, it is envisioned that flexible membrane 140 is made from a biocompatible material to reduce the incidents of adverse reaction by a patient upon contact with the patient's tissue. The flexible membrane 140 can also be made of a transparent material to allow the user to better view the surgical site and surrounding tissue.

With continued reference to FIG. 3, the adjustable ring 150 is disposed at the proximal end 144 of flexible membrane 140. Adjustable ring 150 may be formed from a rigid biomaterial to define a structured opening to passageway 190 which extends from the proximal end 144 of flexible membrane 140 through the body members 110, 120. More specifically, adjustable ring 150 may be disposed through a loop 149 formed at the proximal end 144 of flexible membrane 140. Proximal end 144 may be folded back onto and adhered to flexible membrane 140 to define loop 149 therebetween. Alternatively, adjustable ring 150 may be mechanically engaged with flexible membrane 140 in any other suitable configuration. In some embodiments, ring 150 can be flexible to conform to the contours of the patient's body.

Adjustable ring 150 includes structure to retain the ring in various positions. In the embodiment of FIG. 3, a ratcheting mechanism is provided with overlapping ends 153, 154, each defining a plurality of complementary teeth 153a, 154a, respectively, and notches 153b, 154b, respectively, on opposed surfaces thereof such that teeth 153a are engageable with notches 154b and teeth 154a are engageable with notches 153b to thereby expand or contract adjustable ring 150, as desired, and retain the ring in the select position. Accordingly, adjustable ring 150, and thus proximal end 144 of flexible membrane 140 disposed therearound, may define a minimum diameter wherein ends 153 and 154 of ring 150 are fully overlapping and wherein flexible membrane 140 is substantially un-tensioned, and a maximum diameter, wherein ends 153 and 154 of adjustable ring 150 are only slightly overlapping and wherein flexible membrane 140 is significantly tensioned. As will be described in more detail below, adjusting the ring diameter tensions and slackens the flexible membrane 140, thereby effecting opening and closing (or spreading and retracting) of the passageway 190 defined between body members 110, 120. It is also envisioned that any other suitable adjustable member may be used to adjust/retain adjustable ring 150 between a minimum and a maximum diameter. The adjustable member 140 may include a locking mechanism to lock the flexible member 140 in a plurality of positions, e.g., defining a minimum diameter of ring 150, a maximum diameter of ring 150, and/or a plurality of intermediate diameters.

As mentioned above, the flexible membrane 140 is generally funnel-shaped when tensioned and extends distally and inwardly from the adjustable ring 150, which is disposed at the proximal end 144 of flexible membrane 140, ultimately attaching at a distal end 142 thereof to the body members 110, 120. Moreover, the first and second sections 140a, 140b and end sections 140*d* of flexible membrane 140 may be integral with one another, i.e., formed as a single membrane, or may be formed as separate sections engaged with one another via conventional means. It is envisioned that distal end 142 of flexible membrane 140 be attached or integral with body members 110, 120, such that the passageway 190 extending through access port 100 is isolated from tissue surrounding the incision "I." In a preferred embodiment flexible membrane 140 and body members 110, 120 completely shield the incision "I," to reduce the risk of tissue damage and/or infection during the surgical procedure.

Figure 2A:
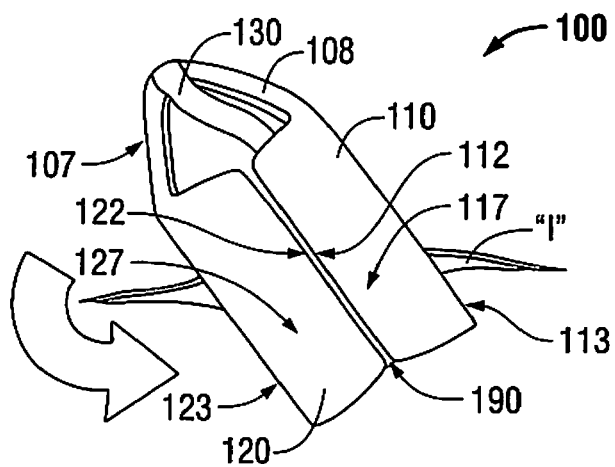
FIG. 2A is a bottom view of the access port of FIG. 1 being rotated into position within the incision in tissue.
Figure 2B:
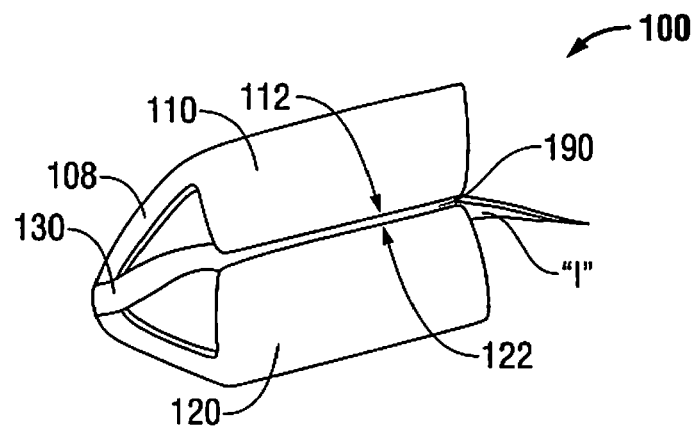
FIG. 2B is a bottom view of the access port of FIG. 1 in position for movement between an approximated and a spread position.

With reference now to FIGS. 2A-2B, horseshoe shaped connector 108 extends from leading ends 114, 124 of body members 110, 120, respectively, of access port 100. Horseshoe shaped connector 108 may be formed integrally with or may be attached to leading ends 114, 124 via suitable means. Horseshoe shaped connector 108 be made from a strong, rigid material to maintain a fixed spatial relation between body members 110, 120. To this end, horseshoe shaped connector 108 may be reinforced to provide further structural support thereto. Horseshoe shaped connector 108 may be configured to maintain outer sides 113, 123 of body members 110, 120, respectively, relatively fixed with respect to one another, while opposed inner sides 112, 122 are flexible with respect to outer sides 113, 123, thereby flexing body members 110, 120. Thus, the passageway 190 extending through access port 100 is expandable between a minimum width, wherein opposed sides 112, 122 of body members 110, 120 are adjacent one another, and a maximum width wherein opposed sides 112, 122 of body members 110, 120 are flexed apart from one another and with respect to the outer sides 113, 123 of body members 110, 120, respectively. As can be appreciated, in the illustrated embodiment, the maximum width of passageway 190 does not exceed the distance between outer sides 113, 123, which are maintained in fixed relation relative to one another by horseshoe shaped connector 108.

A second horseshoe shaped connector (not shown), substantially similar to horseshoe shaped connector 108 may be disposed on the trailing ends 115, 125 of body members 110, 120, respectively, to provide further structural support to body members 110, 120, and more specifically, to outer sides 113, 123 of body members 110, 120, respectively.

Figure 4:
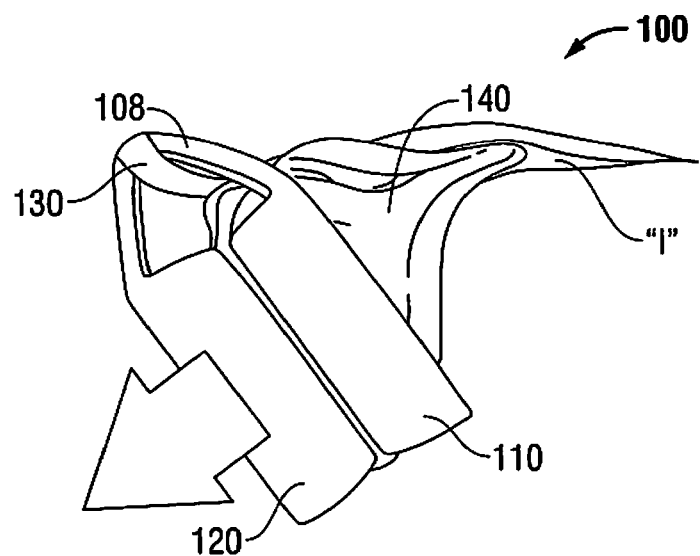
FIG. 4 is a bottom, perspective view of the access port of FIG. 1 showing a flexible membrane extending from the access port and through the incision in tissue.
Figure 5A:
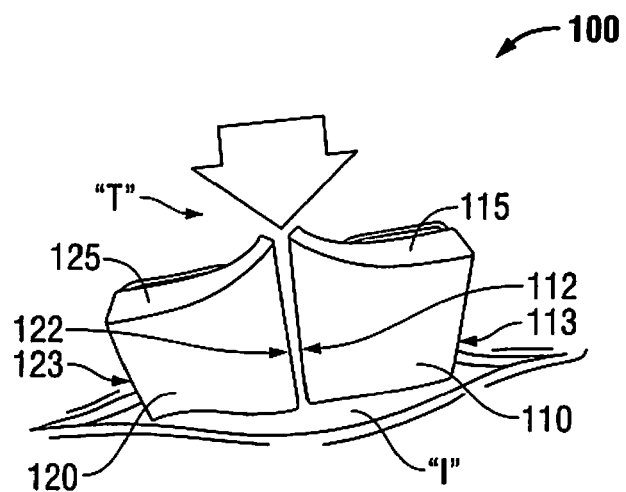
FIG. 5A is a bottom, perspective view of the access port of FIG. 1 shown being removed from the incision in tissue.
Figure 5B:
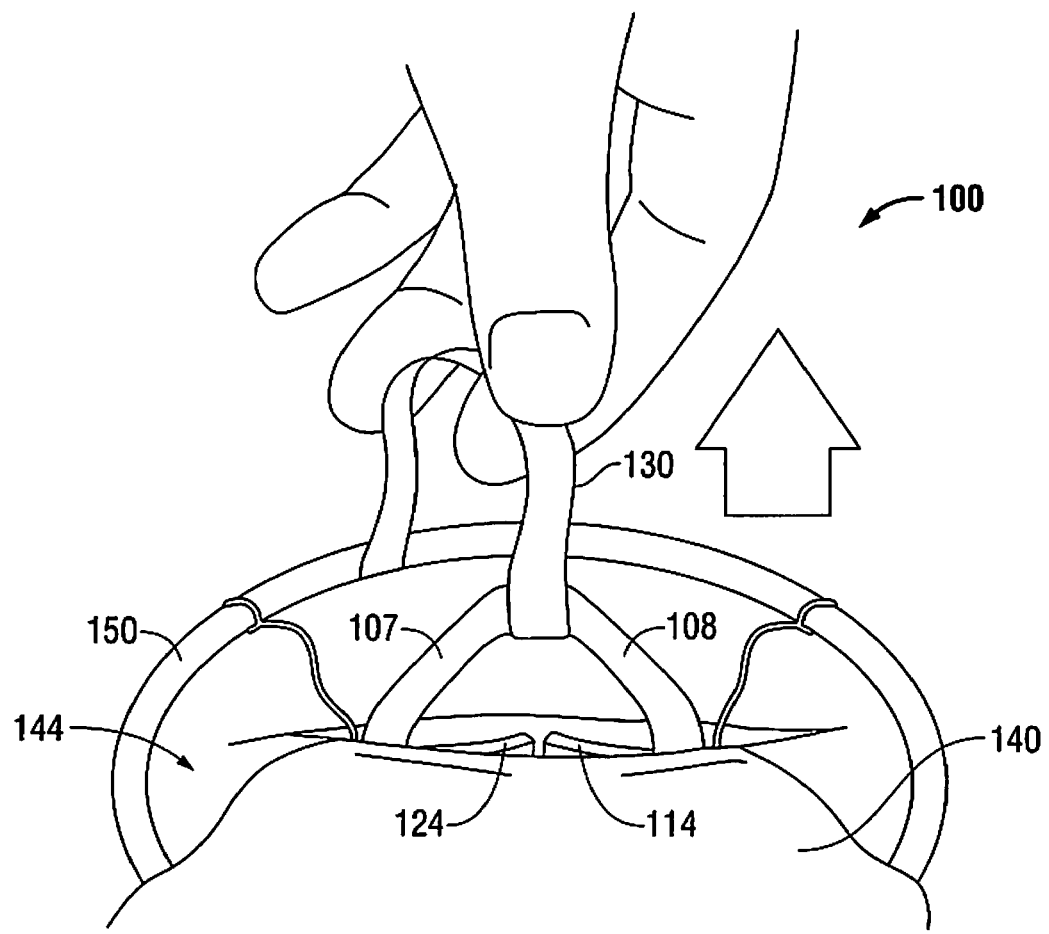
FIG. 5B is a top, perspective view of the access port of FIG. 1 shown being removed from the incision in tissue.

Ribbon 130, as best shown in FIGS. 4 and 5B, is disposed about horseshoe shaped connector 108 and extends therefrom. Ribbon 130 may be adhered to, looped around, or otherwise engaged with horseshoe shaped connector 108. Ribbon 130 has sufficient length to extend proximally from access port 100 out through the incision "I" to be grasped by the user. As will be described in more detail below, ribbon 130 is configured for removal of access port 100 from the incision "I." In some embodiments, ribbon 130 can be provided to facilitate manipulation of access port 100 during the insertion and use of the access port 100. It is envisioned that more than one ribbon 130 may be provided, to further facilitate manipulation of access port 100. Alternatively, or in conjunction with ribbon 130, flexible membrane 140 may be used to manipulate, orient, or position access port 100.

The use and operation of the access port 100 will be now discussed during the course of a minimally invasive thoracic procedure by way of example. As will be appreciated in view of the following, access port 100 is easily inserted, manipulated, and removed from a patient's body. Further, the access port 100 is minimally intrusive, flexible to conform to a patient's anatomy, and provides good visibility into the thoracic cavity "T" (FIG. 3). Additionally, the funnel-shaped, low-profile configuration of access port 100 is particularly advantageous, for example, in the removal, or retrieval, of tissue specimens from within the body.

Initially, an opening, or incision "I," is made in the patient's outer tissue wall of the thoracic body cavity by conventional means. The incision "I" is made between adjacent ribs "R," extending along the intercostal space. In other words, a relatively narrow, elongated incision "I" is made between adjacent ribs "R."

In preparation for insertion through the incision "I," access port 100 is oriented in a vertical position shown in FIG. 1, wherein the horseshoe shaped leading end 107 is distal, or closer to the incision "I," and wherein the trailing ends 115, 125 of body members 110, 120 are proximal, or closer to the user. At this point, the body members 110, 120 are in the approximated position, preferably biased in this position, such that access port 100 is relatively thin and the passageway 190 therethrough defines a minimum width, as described above, or is closed if sides 112 and 122 are in abutment as in some embodiments. This alignment of the access port 100 with the incision "I" allows access port 100 to be inserted through the narrow incision "I" between the adjacent ribs "R" with limited, if any, expansion of the incision and minimal trauma to surrounding tissue. Ribbon 130 extends from horseshoe shaped connector 108 away from the incision "I" such that a portion of ribbon 130 extends from the incision "I," as shown in FIG. 1.

As shown in FIG. 1, the user then grasps the access port 100, e.g., with his/her fingers or with any other suitable surgical tool, and advances the access port 100 distally through the incision "I," led by horseshoe shaped leading end 107. It is envisioned that the leading and trailing ends 114, 124 and 115, 125 of body members 110, 120, respectively, may define a curved configuration to decrease the likelihood of access port 100 "catching" on tissue during insertion and removal of access port 100 from the incision "I." Horseshoe shaped leading end 107 and body members 110, 120 are fully inserted into incision "I," while flexible membrane 140 extends proximally from incision "I."

Once the body members 110, 120 of access port 100 are fully disposed through the incision "I," as shown in FIG. 2A, membrane 140 may be pulled proximally to align the access port 100 for deployment. More specifically, after insertion of access port 100, as can be appreciated, horseshoe shaped leading end 107 is positioned furthest into the body cavity, while trailing ends 115, 125 of body members 110, 120, respectively are closest to the incision "I," i.e., access port 100 is oriented as shown in FIG. 1. With access port 100 fully disposed within the internal body cavity, membrane 140 may be pulled, causing horseshoe shaped leading end 107 to be pulled back towards the incision "I," thereby rotating access port 100. Membrane 140 is pulled until body members 110, 120 of access port 100 are positioned substantially parallel to the surface of tissue through which incision "I" has been made, as shown in FIG. 2A. Lateral translation of membrane 140 may then be effected such that opposed sides 112, 122 of body members 110, 120, respectively, align substantially with the opposing sides of the incision "I" and such that the passageway 190 defined between opposed sides 112, 122 of the body members 110, 120, respectively, aligns with the incision "I," as shown in FIG. 2B. More particularly, the outer sides 113, 123 of body members 110, 120 are positioned adjacent to and distal of the ribs "R," while opposed sides 112, 122, defining passageway 190 therebetween, are positioned adjacent and distal of the incision "I." As mentioned above, one or more ribbons 130 may be provided on horseshoe shaped leading end 107 or at other positions on access port 100 to facilitate removal of access port 100 after completion of the procedure.

It should be noted that, as shown in FIG. 2B, when access port 100 is inserted and positioned within incision "I," access port 100 is oriented such that the concave, outwardly facing surfaces 116, 126 of body members 110, 120 are facing proximally (toward the incision "I") and such that the convex, inwardly facing surfaces 117, 127 of body members 110, 120 are facing distally (toward the thoracic body cavity "T"). As can be appreciated, in this orientation, the opposed sides 112, 122 of body members 110, 120, respectively, extend proximally at least partially toward the incision "I" due to the curved surfaces of body members 110, 120. Flexible membrane 140 extends proximally from opposed sides 112, 122 of body members 110, 120, respectively. More specifically, and although not viewable in FIGS. 2A-2B, flexible membrane 140, having adjustable ring 150 disposed at a proximal end thereof, extends from opposed sides 112, 122 of body members 110, 120 proximally through the incision "I." Ring 150 is positioned adjacent an external surface of tissue and is initially disposed in the minimum, un-tensioned configuration, i.e., wherein ends 153, 154 are substantially overlapping to form a minimum diameter of ring 150. The positioning of ring 150 adjacent the external surface of tissue provides a desirable low-profile configuration that allows for greater maneuverability of surgical instrumentation within access port 100.

Figure 6:
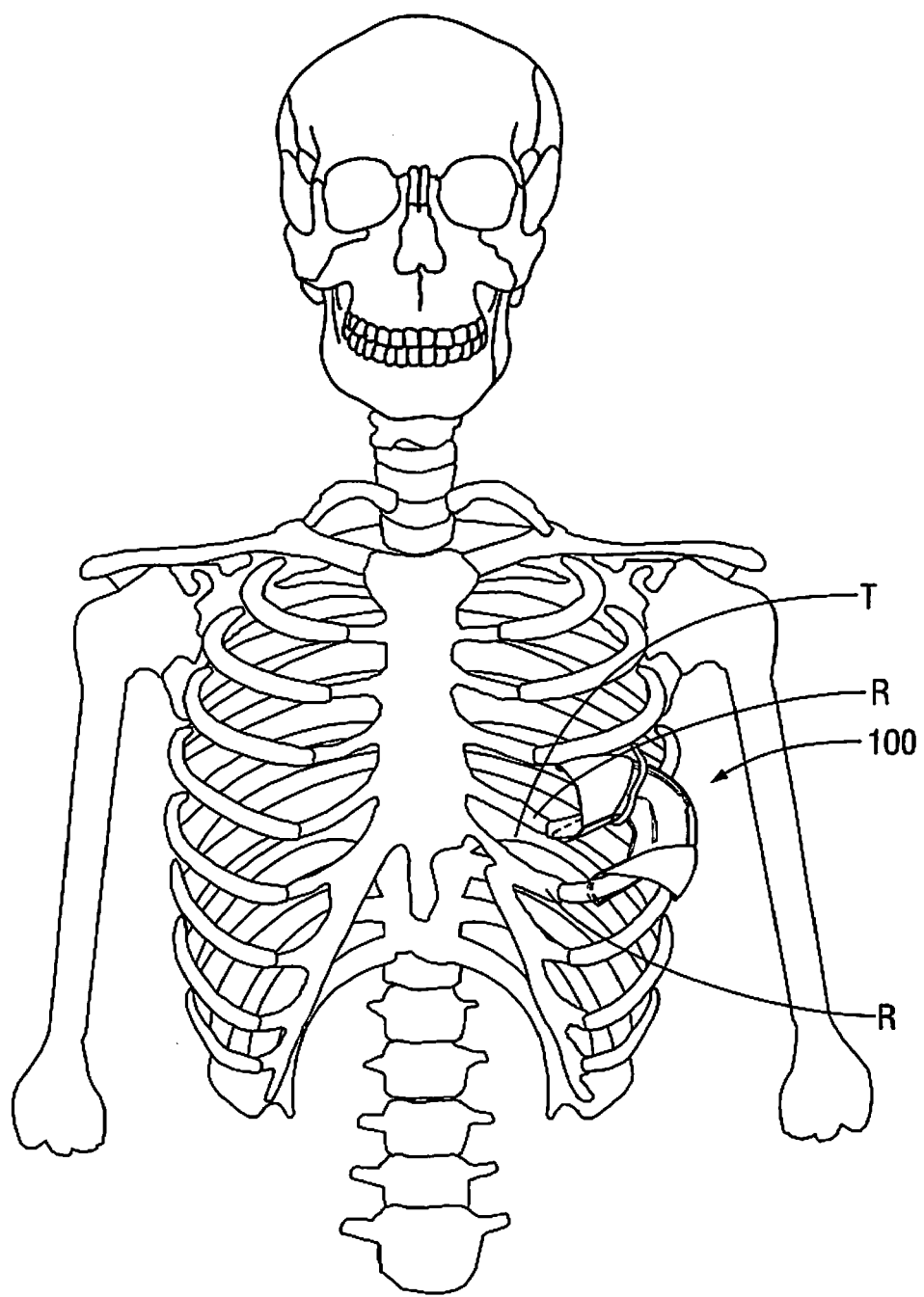
FIG. 6 is a front view illustrating a patient's skeletal structure with surgical access port of FIG. 1 positioned within the intercostal space defined between adjacent ribs.

From the position described above and shown in FIG. 2B, access port 100 may be expanded from the approximated position to the open (spread) position to provide access to an internal body cavity, e.g., the thoracic cavity "T" (FIGS. 3 and 6). In order to expand the access port 100 from the approximated position to the open position, adjustable ring 150 is ratcheted, or expanded, from its minimum diameter to a larger diameter. As can be appreciated, as ring 150 is expanded, ring 150 tensions flexible membrane 140 and pulls flexible membrane 140 proximally through the incision "I," eventually pulling flexible membrane 140 radially outwardly from the incision "I" along the external surface of tissue. As flexible membrane 140 is tensioned and pulled proximally through the incision "I," opposed sides 112 and 122 of body members 110, 120, respectively, are pulled proximally through the incision "I" until flexible membrane 140 is no longer disposed through incision "I" but, rather, completely extends along the external surface of tissue. Body members 110, 120 are thus disposed through the incision "I" with opposed sides 112, 122 extending toward a proximal end of incision "I" and with outer sides 113, 123 extending toward a distal end of incision "I," as shown in FIG. 3. The increased flexibility of body members 110, 120 from outer ends 113, 123 to opposing ends 112, 122 allows body members 110, 120 to be flexed in response to the tensioning and pulling of flexible membrane 140.

Moreover, horseshoe shaped connector 108 helps maintain outer sides 113, 123 in position adjacent and distal of ribs "R." In other words, outer sides 113, 123 are retained within the thoracic cavity "T," distal of the ribs "R," while opposed sides 112, 122 are flexed proximally and apart from one another through the incision "I" in response to the pulling of flexible membrane 140 by the expansion of the adjustable ring 150. Further, it is envisioned that grips (not explicitly shown) may be disposed on the outwardly facing surfaces 116, 126 and, more particularly, lining the saddles 118, 128 of body members 110, 120, respectively, to anchor the body members 110, 120 in position and to prevent slippage.

As shown in FIG. 3, as adjustable ring 150 is moved toward a maximum diameter, outwardly facing surfaces 116, 126 of body members 110, 120 engage the tissue adjacent ribs "R" within saddles 118, 128 and urge the tissue "R" apart from one another to expand the intercostal space. Further, as can be appreciated, as opposed sides 112, 122 of body members 110, 120 are flexed proximally and outwardly from one another to expand tissue adjacent ribs "R," the passageway 190 defined through access port 100 is expanded from the approximated position defining a minimum width to a spread or open position, wherein the passageway 190 defines a larger width, as best shown in FIG. 3. The locking mechanism, e.g., interlocking teeth 153a, 154a and notches 153b, 154b of ends 153, 154 of ring 150, allows access port 100 to be retained in the spread position (FIG. 3). Further, the interlocking teeth 153a, 154a and notches 153b, 154b of ring 150 allow for locking of access port 100 in a plurality of intermediate positions between the approximated position and the spread or open position. Such a feature accommodates different anatomies of different patients, i.e., their intercostal spacing may be different, and accounts for the desirability in some procedures to urge the ribs "R" apart further, while in other procedures to spread the tissue adjacent the ribs to provide access to the internal cavity without increasing the spacing between the adjacent ribs "R."

Once access port 100 is retained or locked in the spread position as described above, surgical instrumentation may be inserted through passageway 190 to perform the surgical procedure therein. As shown in FIG. 3, body members 110, 120 maintain passageway 190 while protecting the incision "I" and the surrounding tissue. Ribs "R" and nerves "N" are protected within saddles 118, 128 by the thickened portions of body members 110, 120 and/or the additional cushioning 119. Flexible membrane 140 extends radially outwardly from incision "I" and protects the external surface of tissue, while adjustable ring 150 maintains access port 100 in the open position. Thus, the incision "I" and surrounding tissue is protected and the tissue adjacent ribs "R" retracted to provide access to the thoracic cavity "T" with minimal pain to the patient and minimal tissue damage. Additionally, as mentioned above, the low-profile configuration of flexible membrane 140 and ring 150 allows for greater access to the thoracic cavity "T," and for greater manipulation of instrumentation disposed through passageway 190

The inwardly facing surfaces 117, 127 of the body members 110, 120, respectively, may be coated with a lubricant, or gel, to aid in the insertion and removal of surgical instrumentation and/or tissue specimens from access port 100.

A textured surface can optionally be placed on the outer (contact) surfaces 166, 126 to increase the grip on the intercostal tissue. The membrane 140 can also optionally have a textured surface to enhance gripping of tissue.

Upon completion of the surgical procedure, adjustable ring 150 is collapsed or "unlocked" and returned to the minimum diameter, thereby un-tensioning flexible membrane 140 and allowing body members 110, 120 to return under the bias to the approximated, or closed, position shown in FIG. 2B, and allowing tissue adjacent ribs "R" to contract back toward their initial position. As body members 110, 120 are returned to the un-flexed, closed position, access port 100 returns to the thin, relatively flat shape characteristic of the approximated position. In this approximated position, access port 100 may be easily removed from the incision "I." More specifically, ribbon 130 may be pulled proximally, thereby pulling horseshoe shaped leading end 107 of access port 100 proximally and rotating access port 100 into removal position, as best shown in FIG. 4. Upon further translation of ribbon 130, as shown in FIGS. 5A-5B, access port 100, lead by horseshoe shaped leading end 107 is translated proximally through the incision "I" until the access port 100 has been completely removed form the incision "I." Finally, the incision "I" may be closed off, e.g., sutured closed.

Although described for use in thoracic procedures, it should also be understood that the access port described herein can be used in other minimally invasive surgical procedures.

Persons skilled in the art will understand that the devices and methods specifically described herein and illustrated in the accompanying figures are non-limiting exemplary embodiments, and that the description, disclosure, and figures should be construed merely exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Accordingly, the subject matter of the present disclosure is not to be limited by what has been particularly shown and described, except as indicated by the appended claims.

What is claimed is:

1. A method of accessing an internal cavity of a patient, comprising:
    forming an opening in the patient's tissue;
    providing an access assembly including:
        a body including first and second body members, each of the first and second body members including an opposed side, an outer side, a leading end and a trailing end, the first and second body members coupled to one another by a connector, the first and second body members moveable with respect to one another between an approximated position, wherein the opposed sides of the first and second body members are closer to one another, and a spread position, wherein the opposed sides of the first and second body members are flexed outwardly and apart from one another to define a passageway therebetween;
        a flexible membrane coupled to the first and second body members and extending therefrom, such that translating the flexible membrane radially outwardly moves the body members from the approximated to the spread position; and
        an adjustable member including an adjustable ring coupled to a proximal end of the flexible membrane;
    inserting the access assembly through the opening in the approximated position such that the body of the access assembly is positioned within an intercostal space defined between adjacent ribs of the patient and such that the flexible membrane extends proximally from the opening;
    rotating the access assembly such that the opposed sides of the first and second body members are aligned with the opening; and
    moving the adjustable ring from a first position, wherein the adjustable ring defines a minimum diameter, to a second position, wherein the adjustable ring defines a larger diameter to translate the flexible membrane radially outwardly and move the opposed sides of the first and second body members from the approximated position to the spread position, thereby expanding the intercostal space.

2. The method of claim 1, wherein providing the access assembly includes providing at least one ribbon coupled to the connector to facilitate at least one of translation of the membrane or rotation of the access assembly.

3. The method of claim 2, further comprising translating the access assembly proximally via the leading ends of the first and second body members to remove the access assembly from the opening.

4. The method of claim 3, wherein removing the access assembly includes pulling the ribbon proximally to withdraw the body of the access assembly from the opening.

5. The method of claim 1, further comprising passing at least one of surgical instrumentation or a tissue specimen through the access assembly.

6. The method of claim 1, wherein inserting the access assembly includes positioning the access assembly such that cushioning members secured to outer surfaces of the first and second body members contact adjacent tissue portions defining the opening.

7. The method of claim 1, further comprising locking the adjustable ring in the second position to overcome a biasing force urging the first and second body members towards the approximated position to thereby maintain the passageway defined between the first and second body members.

8. The method of claim 7, wherein locking the adjustable ring in the second position includes positioning a plurality of teeth defined in a first surface of the adjustable ring within corresponding notches defined a second surface of the adjustable ring.

9. A method of accessing an internal cavity of a patient, comprising:
    forming an opening in the patient's tissue;
    positioning a body of an access assembly within the opening, the body including first and second members, the first and second members including opposed inner sides;
    expanding an adjustable ring to apply tension to a membrane extending between the adjustable ring and the opposed inner sides of the first and second members of the body of the access assembly, to cause the first and second members to move and be at least partially received within the opening, to thereby expand the opening and create a passageway between the opposed inner sides of the first and second members of the body and extending through the access assembly; and
    applying a force to a ribbon secured to the body of the access assembly to withdraw the body of the access assembly from the opening, and wherein applying the force to the ribbon includes pulling a horseshoe-shaped member connecting the first and second members of the body towards the opening.

10. The method of claim 9, wherein expanding the adjustable ring includes pivoting the first and second members from an approximated position, wherein the inner sides of the first and second members are positioned in substantially adjacent relation, to a spread position, wherein the inner sides of the first and second members are separated from each other to thereby define the passageway extending through the access assembly.

11. The method of claim 10, including locking the adjustable ring in an expanded position to overcome a biasing force urging the first and second members of the body towards the approximated position to thereby maintain the passageway extending through the access assembly.

12. The method of claim 11, wherein locking the adjustable ring includes positioning a plurality of teeth defined in a first surface of the adjustable ring within corresponding notches defined a second surface of the adjustable ring.

13. The method of claim 10, wherein pivoting the first and second members includes pivoting the first and second members about outer sides thereof.

14. The method of claim 9, wherein expanding the adjustable ring includes drawing the membrane radially outward.

15. The method of claim 9, wherein positioning the body of the access assembly includes introducing the body within an intercostal space defined between adjacent ribs of the patient such that the membrane extends proximally from the opening, and the adjustable ring is positioned externally of the patient.

16. The method of claim 9, wherein positioning the body of the access assembly includes rotating the body such that the inner sides of the first and second members are aligned with the opening.

17. The method of claim 9, wherein positioning the body of the access assembly includes arranging the access assembly such that cushioning members secured to outer surfaces of the first and second members of the body contact adjacent tissue portions defining the opening.

18. The method of claim 9, including passing surgical instrumentation and/or a tissue specimen through the access assembly.

19. A surgical method, comprising:
    establishing a tissue passage through tissue to access an underlying body cavity of a subject;
    positioning an access body relative to the tissue passage, the access body including first and second members interconnected by a connector member, the first and second members including opposed inner sides and having a flexible membrane segment mounted adjacent each opposed inner side;
    advancing the access body within the tissue passage to position the connector member and the first and second members within the body cavity; and
    applying tension to the flexible membrane segments to cause the opposed inner sides of the first and second members to be displaced relative to each other and drawn within the tissue passage such that the first and second members engage tissue portions defining the tissue passage to expand the tissue passage while an access passageway is created between the first and second members for introduction of an object.

20. The surgical method of claim 19 wherein applying tension to the flexible membrane segments includes pivoting the first and second members to enter the tissue passage.

21. The surgical method of claim 19 wherein the connector member extends between outer sides of the first and second members and wherein applying tension to the flexible membrane segments includes pivoting the first and second members about respective outer sides of the first and second members.

22. The surgical method of claim 19 wherein advancing the access body includes introducing the connector member within the tissue passage and advancing the connector member such that the connector member enters into the body cavity followed by entrance of the first and second members.

23. The surgical method of claim 19 wherein the first and second members of the body are formed of a semi-rigid material.

24. The surgical method of claim 19 wherein applying tension to the flexible membrane segments including moving an adjustable ring coupled to the flexible membrane segments from a first position, wherein the adjustable ring defines a minimum diameter, to a second position, wherein the adjustable ring defines a larger diameter to translate the flexible membrane segments radially outwardly and move the opposed inner sides of the first and second members from an approximated position to a spread position, thereby expanding the tissue passage.

* * * * *